United States Patent
Li

(10) Patent No.: US 9,518,710 B2
(45) Date of Patent: Dec. 13, 2016

(54) ELECTRONIC FLAMELESS CANDLE

(71) Applicant: Xiaofeng Li, Shenzhen (CN)

(72) Inventor: Xiaofeng Li, Shenzhen (CN)

(*) Notice: Subject to any disclaimer, the term of this patent is extended or adjusted under 35 U.S.C. 154(b) by 0 days.

(21) Appl. No.: 15/158,508

(22) Filed: May 18, 2016

(65) Prior Publication Data

US 2016/0258584 A1  Sep. 8, 2016

Related U.S. Application Data

(63) Continuation of application No. 14/213,287, filed on Mar. 14, 2014, now Pat. No. 9,360,181.

(Continued)

(51) Int. Cl.

| | | |
|---|---|---|
| *F21V 21/00* | (2006.01) | |
| *F21S 10/04* | (2006.01) | |
| *F21V 33/00* | (2006.01) | |
| *F21S 9/02* | (2006.01) | |
| *F21V 23/04* | (2006.01) | |
| *F21S 6/00* | (2006.01) | |
| *A61L 9/03* | (2006.01) | |
| *F21Y 101/02* | (2006.01) | |

(52) U.S. Cl.
CPC ............... *F21S 10/04* (2013.01); *A61L 9/03* (2013.01); *F21S 6/001* (2013.01); *F21S 9/02* (2013.01); *F21V 23/04* (2013.01); *F21V 33/0088* (2013.01); *F21V 33/0092* (2013.01); *A61L 2209/12* (2013.01); *A61L 2209/133* (2013.01); *F21Y 2101/02* (2013.01)

(58) Field of Classification Search
CPC .............. F21S 10/04; F21S 9/02; F21S 6/001; F21V 33/0088; F21V 33/0092; F21V 23/04; A61L 9/03

See application file for complete search history.

(56) References Cited

U.S. PATENT DOCUMENTS

| 782,156 A | 2/1905 | Meeker |
|---|---|---|
| 817,772 A | 4/1906 | Helmer |

(Continued)

FOREIGN PATENT DOCUMENTS

| CN | 1030823 | 2/1989 |
|---|---|---|
| CN | 2551859 | 5/2003 |

(Continued)

OTHER PUBLICATIONS

U.S. Appl. No. 15/061,648, filed Mar. 4, 2016, Li.

(Continued)

*Primary Examiner* — Thomas M Sember
(74) *Attorney, Agent, or Firm* — Perkins Coie LLP

(57) ABSTRACT

An electronic flameless candle including a body having a top surface, a bottom surface, a sidewall between the top surface and the bottom surface, and a cavity defined by the top surface, the bottom surface and the sidewall, the body configured in shape and size to simulate a true flame candle. The candle may also include a light source operably connected to the body, the light source electrically operated to illuminate in a way that simulates a natural flicker of a real candle flame. The candle may also include a scent component, operably connected to the body, the scent component configured to emit a scent when heated and/or a sensor component, operably connected to the body, the sensor component configured to sense an environmental condition and affect a mode of the light source upon the sensing of the environmental condition.

29 Claims, 16 Drawing Sheets

Related U.S. Application Data

(60) Provisional application No. 61/798,527, filed on Mar. 15, 2013, provisional application No. 61/798,348, filed on Mar. 15, 2013, provisional application No. 61/798,053, filed on Mar. 15, 2013.

(56) References Cited

U.S. PATENT DOCUMENTS

| | | |
|---|---|---|
| 1,507,371 A | 8/1924 | Goodridge |
| 1,842,167 A | 1/1932 | Hall |
| 1,955,042 A | 4/1934 | Work |
| D102,561 S | 12/1936 | Lamb |
| 2,435,811 A | 2/1948 | Waters |
| 2,976,450 A | 3/1961 | Benoliel |
| 2,984,032 A | 5/1961 | Cornell |
| 3,233,093 A | 2/1966 | Gerlat |
| 3,384,774 A | 5/1968 | English |
| 3,425,157 A | 2/1969 | Hartsock |
| 3,514,660 A | 5/1970 | Kopelman |
| 3,603,013 A | 9/1971 | Gardiner |
| 3,639,749 A | 2/1972 | Beckman |
| 3,681,588 A | 8/1972 | Lee |
| 3,814,973 A | 6/1974 | Thouret et al. |
| 3,890,085 A | 6/1975 | Andeweg |
| 4,026,544 A | 5/1977 | Plambeck et al. |
| 4,328,534 A | 5/1982 | Abe |
| 4,477,249 A | 10/1984 | Ruzek et al. |
| 4,550,363 A | 10/1985 | Sandell |
| 4,551,794 A | 11/1985 | Sandell |
| 4,617,614 A | 10/1986 | Lederer |
| 4,777,571 A | 10/1988 | Morgan |
| 4,866,580 A | 9/1989 | Blackerby |
| 4,965,707 A | 10/1990 | Butterfield |
| 5,097,180 A | 3/1992 | Ignon et al. |
| 5,381,325 A | 1/1995 | Messana |
| 5,707,282 A | 1/1998 | Clements et al. |
| 5,924,784 A | 7/1999 | Chliwnyj et al. |
| 6,198,229 B1 | 3/2001 | McCloud |
| 6,257,755 B1 | 7/2001 | Sevelle |
| 6,302,555 B1 | 10/2001 | Bristow |
| 6,312,137 B1 | 11/2001 | Hsieh |
| 6,454,425 B1 | 9/2002 | Lin |
| 6,461,011 B1 | 10/2002 | Harrison |
| 6,511,219 B2 | 1/2003 | Sevelle |
| D486,924 S | 2/2004 | Skradski et al. |
| 6,688,752 B2 | 2/2004 | Moore |
| 6,712,493 B2 | 3/2004 | Tell et al. |
| 6,757,487 B2 | 6/2004 | Martin et al. |
| 6,781,270 B2 | 8/2004 | Long |
| 6,953,401 B2 | 10/2005 | Starr |
| 6,955,440 B2 | 10/2005 | Niskanen |
| 6,966,665 B2 | 11/2005 | Limburg et al. |
| 7,029,146 B2 | 4/2006 | Kitchen |
| 7,080,472 B2 | 7/2006 | Schroeter et al. |
| 7,083,315 B2 | 8/2006 | Hansler et al. |
| 7,093,949 B2 | 8/2006 | Hart et al. |
| 7,111,421 B2 | 9/2006 | Corry et al. |
| 7,118,243 B2 | 10/2006 | McCavit et al. |
| 7,125,142 B2 | 10/2006 | Wainwright |
| 7,159,994 B2 | 1/2007 | Schnuckle et al. |
| D545,458 S | 6/2007 | Jensen |
| 7,261,455 B2 | 8/2007 | Schnuckle et al. |
| 7,300,179 B1 | 11/2007 | LaDuke et al. |
| 7,305,783 B2 | 12/2007 | Mix et al. |
| D567,993 S | 4/2008 | Shiu |
| 7,360,935 B2 | 4/2008 | Jensen et al. |
| D576,317 S | 9/2008 | Jensen |
| D589,176 S | 3/2009 | Huang et al. |
| D599,491 S | 9/2009 | Luo |
| 7,633,232 B2 | 12/2009 | Wong |
| 7,686,471 B2 | 3/2010 | Reichow |
| 7,824,627 B2 | 11/2010 | Michaels et al. |
| 7,828,462 B2 | 11/2010 | Jensen et al. |
| 7,837,355 B2 | 11/2010 | Schnuckle |
| 8,070,319 B2 | 12/2011 | Schnuckle et al. |
| 8,081,872 B2 | 12/2011 | Wang |
| 8,132,936 B2 | 3/2012 | Patton et al. |
| 8,210,708 B2 | 7/2012 | Hau et al. |
| 8,235,558 B1 | 8/2012 | Lauer |
| 8,454,190 B2 | 6/2013 | Hau et al. |
| 8,534,869 B2 | 9/2013 | Patton et al. |
| 8,696,166 B2 | 4/2014 | Patton et al. |
| 8,789,986 B2 | 7/2014 | Li |
| 8,894,261 B2 | 11/2014 | Chen |
| 8,926,137 B2 | 1/2015 | Li |
| 8,998,461 B2 | 4/2015 | Gutstein et al. |
| 9,033,553 B2 | 5/2015 | Li |
| 9,052,078 B2 | 6/2015 | Sheng |
| 2001/0033488 A1 | 10/2001 | Chliwnyj et al. |
| 2002/0080601 A1 | 6/2002 | Meltzer |
| 2003/0041491 A1 | 3/2003 | Mix |
| 2003/0053305 A1 | 3/2003 | Lin |
| 2003/0072154 A1 | 4/2003 | Moore |
| 2004/0114351 A1 | 6/2004 | Stokes et al. |
| 2004/0165374 A1 | 8/2004 | Robinson |
| 2004/0223326 A1 | 11/2004 | Wainwright |
| 2005/0007779 A1 | 1/2005 | Nozawa |
| 2005/0097792 A1 | 5/2005 | Naden |
| 2005/0169812 A1 | 8/2005 | Helf |
| 2005/0196716 A1 | 9/2005 | Haab |
| 2005/0285538 A1 | 12/2005 | Jaworski et al. |
| 2006/0034079 A1 | 2/2006 | Schnuckle et al. |
| 2006/0034100 A1 | 2/2006 | Schnuckle et al. |
| 2006/0101681 A1 | 5/2006 | Hess et al. |
| 2006/0120080 A1 | 6/2006 | Sipinski et al. |
| 2006/0146544 A1 | 7/2006 | Leung |
| 2007/0002560 A1 | 1/2007 | Gutstein et al. |
| 2007/0127249 A1 | 6/2007 | Medley et al. |
| 2007/0154857 A1 | 7/2007 | Cho |
| 2007/0159422 A1 | 7/2007 | Blandino et al. |
| 2007/0236947 A1 | 10/2007 | Jensen et al. |
| 2008/0074875 A1 | 3/2008 | Jensen et al. |
| 2008/0112154 A1 | 5/2008 | Reichow |
| 2008/0129226 A1 | 6/2008 | DeWitt et al. |
| 2008/0130266 A1 | 6/2008 | DeWitt et al. |
| 2009/0059596 A1 | 3/2009 | Lederer |
| 2009/0135586 A1 | 5/2009 | Yang |
| 2010/0079999 A1 | 4/2010 | Schnuckle |
| 2010/0134022 A1 | 6/2010 | Gutstein et al. |
| 2011/0019422 A1 | 1/2011 | Schnuckle |
| 2011/0110073 A1 | 5/2011 | Schnuckle et al. |
| 2011/0127914 A1 | 6/2011 | Patton |
| 2011/0204828 A1 | 8/2011 | Moody et al. |
| 2011/0317403 A1 | 12/2011 | Fournier et al. |
| 2012/0134157 A1 | 5/2012 | Li |
| 2013/0050985 A1 | 2/2013 | Kwok et al. |
| 2013/0163249 A1 | 6/2013 | Miura |
| 2013/0265748 A1 | 10/2013 | Hau et al. |
| 2014/0211499 A1 | 7/2014 | Fong et al. |
| 2014/0254148 A1 | 9/2014 | Fournier |
| 2014/0268652 A1 | 9/2014 | Li |
| 2014/0268704 A1 | 9/2014 | Yang |
| 2014/0286024 A1 | 9/2014 | Li |
| 2014/0313694 A1 | 10/2014 | Patton |
| 2014/0362592 A1 | 12/2014 | Lee |
| 2015/0036348 A1 | 2/2015 | Dong |
| 2015/0109786 A1 | 4/2015 | Li |
| 2015/0124442 A1 | 5/2015 | Ding |
| 2015/0233538 A1 | 8/2015 | Sheng |
| 2015/0308643 A1 | 10/2015 | Huang |
| 2015/0369431 A1 | 12/2015 | Li |
| 2015/0369432 A1 | 12/2015 | Li |
| 2016/0040844 A1 | 2/2016 | Patton |
| 2016/0047517 A1 | 2/2016 | Li |
| 2016/0057829 A1 | 2/2016 | Li |
| 2016/0109082 A1 | 4/2016 | Li |
| 2016/0109083 A1 | 4/2016 | Li |

FOREIGN PATENT DOCUMENTS

| | | |
|---|---|---|
| CN | 2562059 Y | 7/2003 |
| CN | 1530142 A | 9/2004 |
| CN | 1646177 A | 7/2005 |
| CN | 2854329 Y | 1/2007 |

(56) References Cited

FOREIGN PATENT DOCUMENTS

| | | | |
|---|---|---|---|
| CN | 2888274 | Y | 4/2007 |
| CN | 200940808 | Y | 8/2007 |
| CN | 201011621 | Y | 1/2008 |
| CN | 201059432 | Y | 5/2008 |
| CN | 201103952 | Y | 8/2008 |
| CN | 201159425 | Y | 12/2008 |
| CN | 101408284 | A | 4/2009 |
| CN | 201235095 | Y | 5/2009 |
| CN | 201418887 | Y | 3/2010 |
| CN | 201533921 | U | 7/2010 |
| CN | 101865413 | A | 10/2010 |
| CN | 201643048 | U | 11/2010 |
| CN | 102147095 | A | 8/2011 |
| CN | 102748589 | A | 10/2012 |
| CN | 203273670 | U | 11/2013 |
| CN | 203442498 | U | 2/2014 |
| CN | 203517611 | U | 4/2014 |
| CN | 203571618 | U | 4/2014 |
| DE | 1489617 | A1 | 5/1969 |
| DE | 102012206988 | A1 | 10/2013 |
| EP | 0138786 | A1 | 4/1985 |
| EP | 0855189 | A2 | 7/1998 |
| EP | 1838110 | A1 | 9/2007 |
| EP | 2587127 | A1 | 5/2013 |
| GB | 2323159 | A | 9/1998 |
| GB | 2379731 | A | 3/2003 |
| GB | 2385413 | A | 8/2003 |
| GB | 2455598 | A | 6/2009 |
| JP | H0652709 | | 2/1994 |
| JP | H1057464 | A | 3/1998 |
| JP | 2000284730 | A | 10/2000 |
| JP | 2008180755 | A | 8/2008 |
| WO | WO-8202756 | A1 | 8/1982 |
| WO | WO-8503561 | A1 | 8/1985 |
| WO | WO-8704506 | A1 | 7/1987 |
| WO | WO-9625624 | A1 | 8/1996 |
| WO | WO-0192780 | | 12/2001 |
| WO | WO-03011349 | | 2/2003 |
| WO | WO-2006020839 | A2 | 2/2006 |
| WO | WO-2008092753 | A2 | 8/2008 |
| WO | WO-2012000418 | A1 | 1/2012 |
| WO | WO-2013020263 | A2 | 2/2013 |

OTHER PUBLICATIONS

U.S. Appl. No. 15/132,548, filed Apr. 19, 2016, Li.
U.S. Appl. No. 15/150,057, filed May 9, 2016, Li.
U.S. Appl. No. 15/137,951, filed Apr. 25, 2016, Li.
U.S. Appl. No. 15/145,739, filed May 3, 2016, Li.
U.S. Appl. No. 14/588,507, filed Jan. 2, 2015, Li.
U.S. Appl. No. 14/925,893, filed Oct. 28, 2015, Li.
U.S. Appl. No. 61/101,611 to Schnuckle, filed Sep. 30, 2008.
U.S. Appl. No. 61/293,516 to Patton, filed Jan. 8, 2010.
International Search Report and Written Opinion for PCT Application No. PCT/CN/2014/073557 mailed Jul. 2, 2014.
International Search Report for PCT Application No. PCT/US2009/054401 mailed Oct. 26, 2009.
EP Search Report for European Patent Application No. 12185984.7 mailed Dec. 14, 2012.
Engineer's Handbook (Epoxy definition), http://engineershandbook.com/Materials/epoxy.htm, Jul. 18, 2013.
Nagashima, H. et al., "Introduction to Chaos, Physics and Mathematics of Chaotic Phenomena," Institute of Physics Publishing, 1999.
Definition of "Electromagnet" in the Encarta World English Dictionary, Aug. 1999.
Lab M3: The Physical Pendulum, Physics 1140—Experimental Physics, Course Laboratory Instructions, 2000.

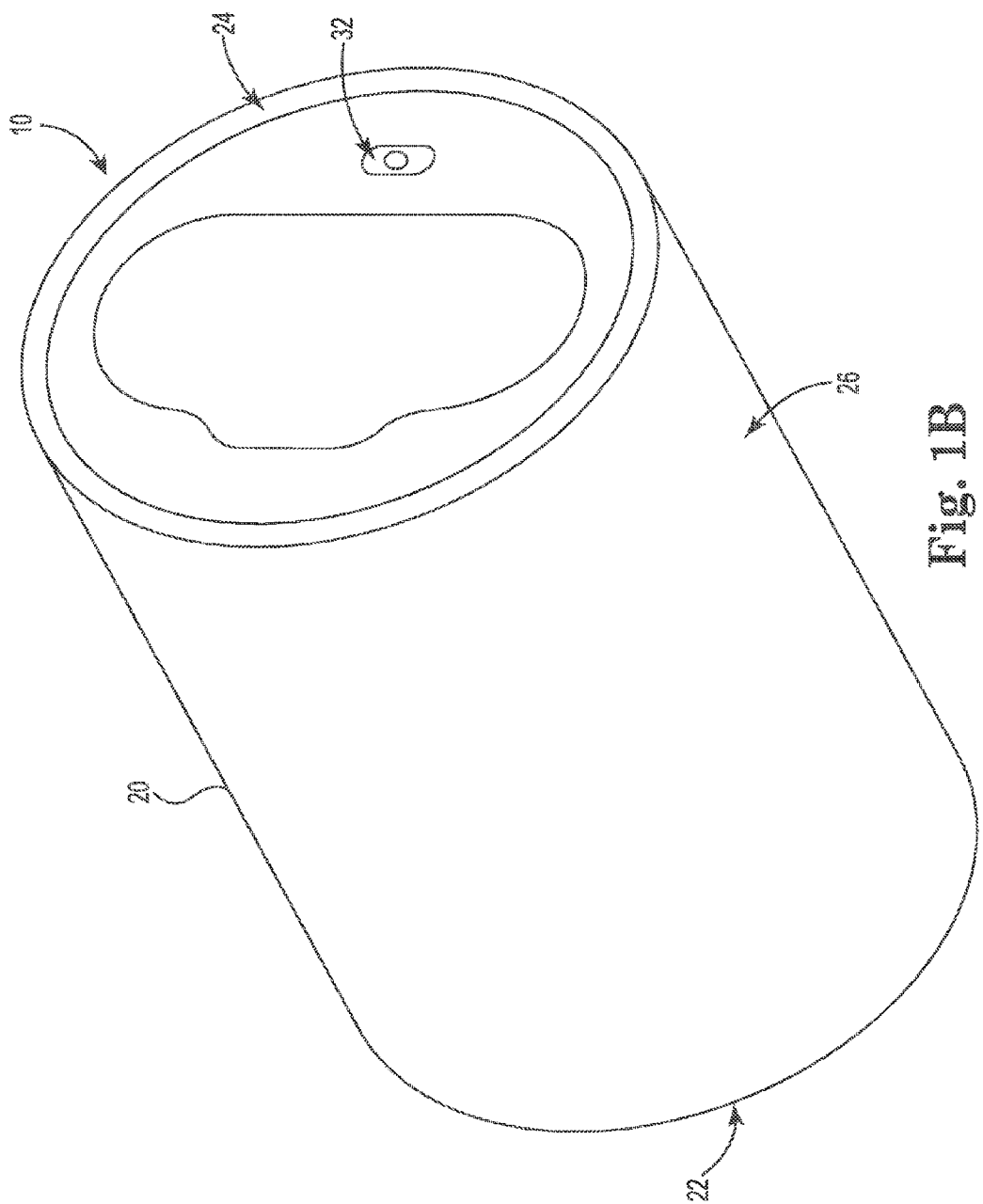

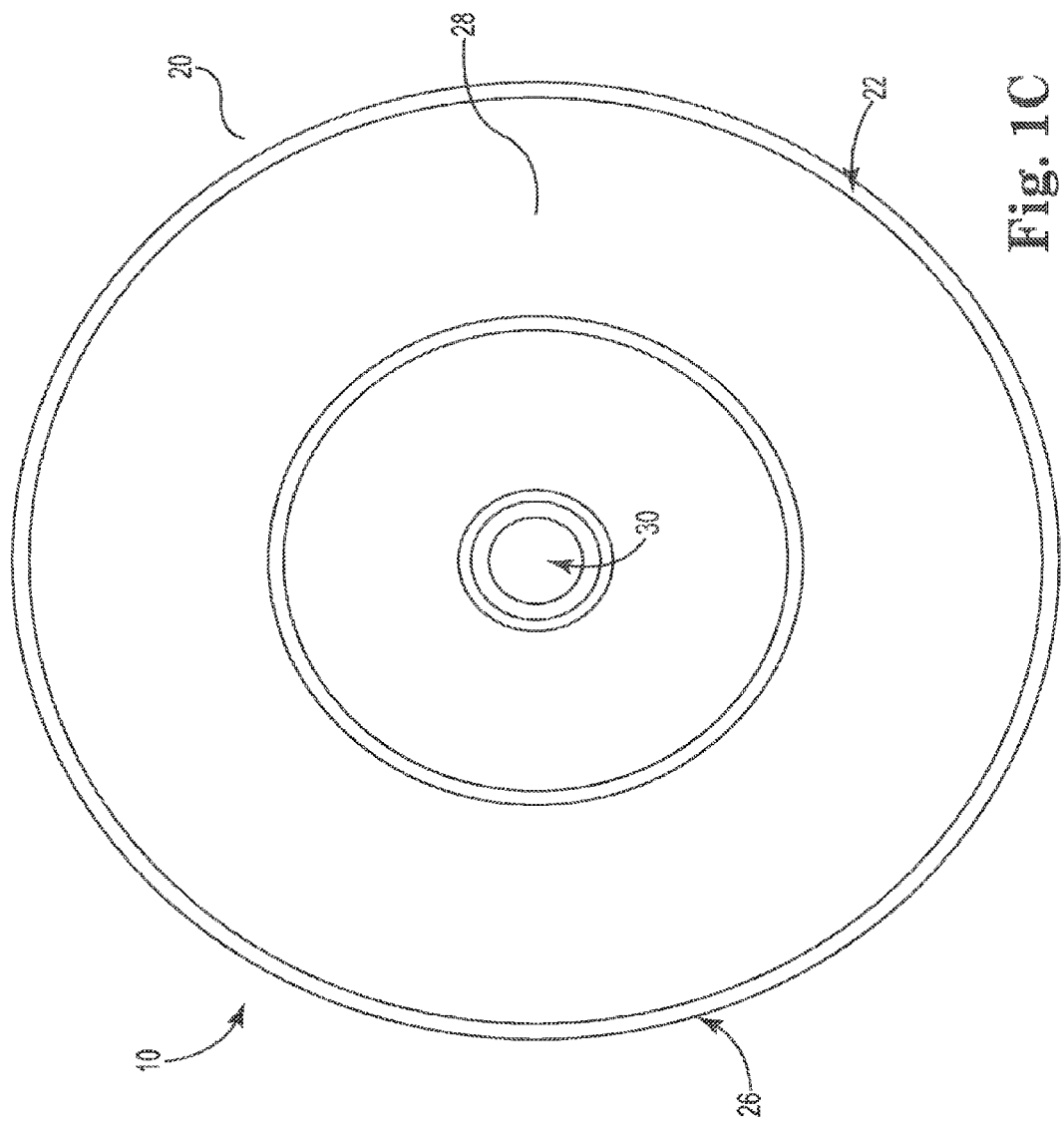

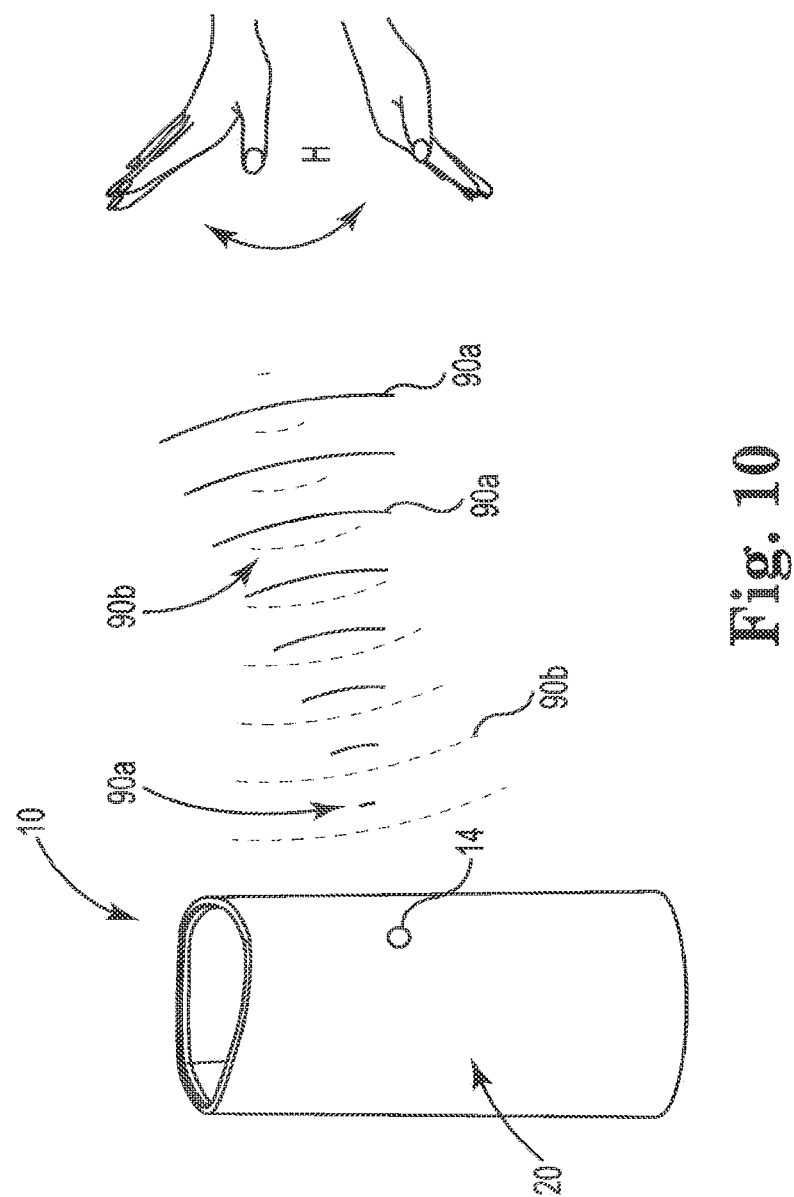

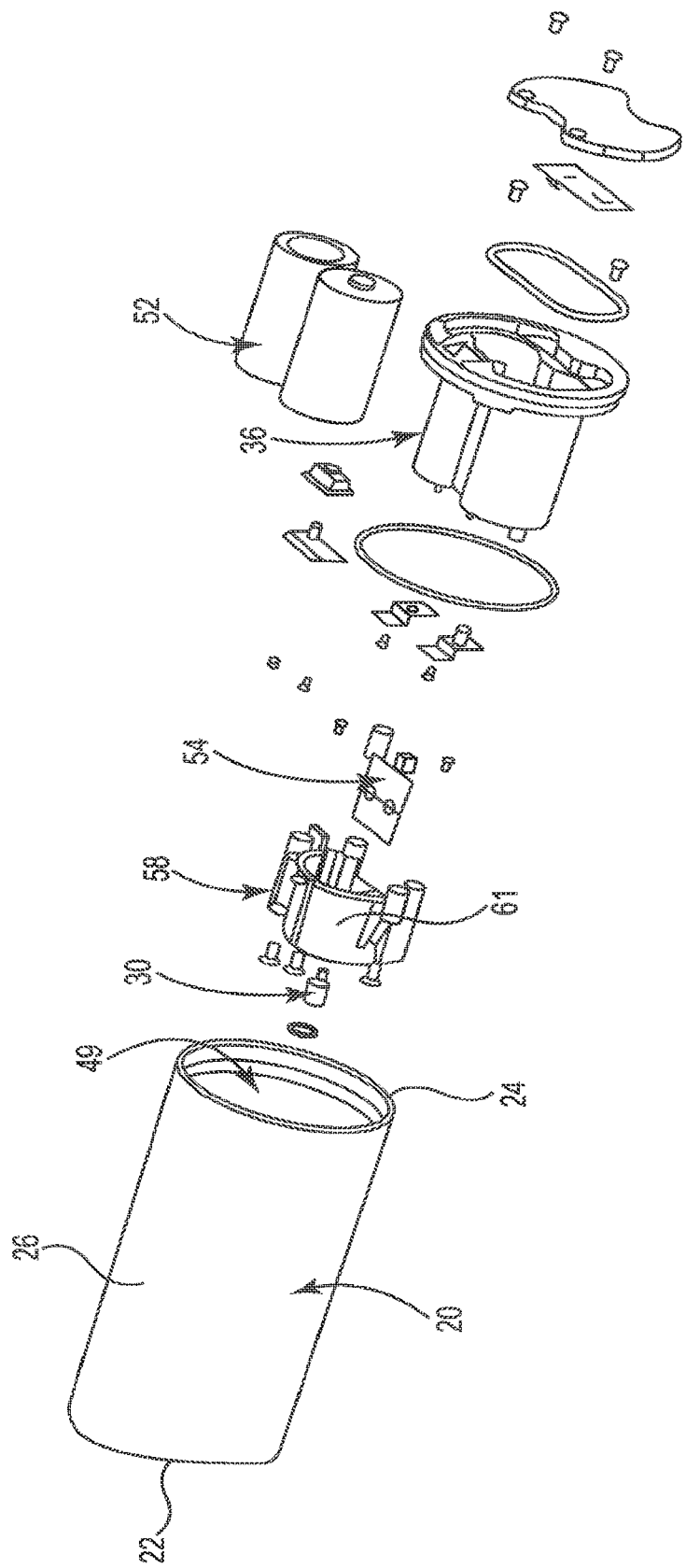

ELECTRONIC FLAMELESS CANDLE

CROSS-REFERENCE TO RELATED APPLICATION(S)

The present application is a continuation of U.S. patent application Ser. No. 14/213,287, filed Mar. 14, 2014, now U.S. Pat. No. 9,360,181, which claims the benefit of U.S. provisional patent applications: Ser. No. 61/798,527, filed on Mar. 15, 2013, entitled "Flameless Candle," Ser. No. 61/798,348, filed on Mar. 15, 2013, entitled "Scented Flameless Candle," and Ser. No. 61/798,053, filed on Mar. 15, 2013, entitled "Flameless Candle with Motion Sensor," the disclosures of each of which are hereby incorporated by reference herein in their entireties.

TECHNICAL FIELD

The present disclosure relates to novel and advantageous flameless candles. Particularly, the present disclosure relates to novel and advantageous flameless candles simulating a realistic flame-like flicker, are capable of emitting a scent, and/or allow users to more easily control the candles' operations.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Traditional true flame candles, when lit, provide a pleasant ambience in many homes and businesses. Traditional candles may also be scented, adding a pleasant aroma. While the wax typically has a scent, even when the candle is not lit, this scent may be amplified when the candle is lit. Traditional candles however, provide a variety of hazards including risk of fire, damage to surfaces caused by hot wax, and the possible emission of soot. Flameless candles have become increasingly popular alternatives to traditional candles. With no open flame or hot melted wax, flameless candles provide a longer-lasting, safe, and clean alternative. There are flameless candles available that use incandescent lamps or light-emitting diodes (LEDs) as a light source. However, such flameless candles are easily distinguishable from their traditional candle counterparts. One problem is that flameless candles generally cannot suitably simulate the natural flicker of an actual flame as viewed by the naked eye. Another problem is flameless candles have not been able to provide a scented feature that simulates the desired scented feature of a traditional candle, particularly when lit. In addition, flameless candles typically have one or more switches on the base of the candle to turn the candle on, off, or into a flicker mode. This requires the user to awkwardly or inelegantly take the candle off its resting place.

Thus, there is a need in the art for a flameless candle that is aesthetically similar to a traditional candle. More particularly, there is a need for a flameless candle that emits a more natural, flame-like flicker of light, is capable of emitting a scent, and allows the user to relatively easily control the candle's operations.

SUMMARY

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one embodiment, relates to an electronic flameless candle. The candle may include a body having a top surface, a bottom surface, a sidewall between the top surface and the bottom surface, and a cavity defined by the top surface, the bottom surface and the sidewall, the body configured in shape and size to simulate a true flame candle. The candle may also include a light source operably connected to the body, the light source electrically operated to illuminate in a way that simulates a natural flicker of a real candle flame.

The present disclosure, in another embodiment, relates to an electronic flameless candle. The candle may include a body having a top surface, a bottom surface, a sidewall between the top surface and the bottom surface, and a body cavity defined by the top surface, the bottom surface and the sidewall, the body configured in shape and size to simulate a true flame candle. The candle may also include a light source operably connected to the body, and a scent component, operably connected to the body, the scent component configured to emit a scent when heated.

The present disclosure, in another embodiment, relates to an electronic flameless candle. The candle may include a body having a top surface, a bottom surface, a sidewall between the top surface and the bottom surface, and a cavity defined by the top surface, the bottom surface and the sidewall, the body configured in shape and size to simulate a true flame candle. The candle may also include a light source operably configured in the body, and a sensor component, operably connected to the body, the sensor component configured to sense an environmental condition and affect a mode of the light source upon the sensing of the environmental condition.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 1B is a bottom perspective view of a flameless pillar candle, according to an embodiment of the present disclosure.

FIG. 1C shows a top view of a flameless candle, according to an embodiment of the present disclosure.

FIG. 10 illustrates how a motion sensor functions with a flameless pillar candle, according to an embodiment of the present disclosure.

FIG. 11 is an exploded view of a flameless candle, according to an embodiment of the present disclosure.

DETAILED DESCRIPTION

The present disclosure relates to novel and advantageous flameless candles. Particularly, the present disclosure relates to novel and advantageous flameless candles simulating a realistic flame-like flicker, are capable of emitting a scent, and/or allow users to more easily control the candles' operations.

The present disclosure relates, in some embodiments, to a flameless candle that uses, in at least one embodiment, a LED light source to provide a natural, flame-like flicker of light. The flameless candle may include a body having a top surface, a bottom surface upon which the body rests, and a sidewall between the bottom surface and the top surface. One or more control switches may be located on the top surface, the bottom surface, or on the sidewall. Each of these control switches may provide a variety of functions when activated separately or together, including, but not limited to, turning the light source on or off, operating the light source in static or random flicker mode, changing the color of the light, dimming or brightening of the light source, or operating a timer to the light on or off. The natural flicker may be created by a circuit board which provides a signal to the light. The signal may be comprised of random frequencies and amplitudes of current. The circuit board may also control pulse-width modulation and the frequency and duty ratio of the signal received by the light. The signal transmitted randomly to one or more of the diodes of the LED may cause the LED to produce a natural "flicker" of light to the human eye. In various embodiments, the flameless candle may alternatively or additionally include a scent diffusing component to diffuse a pleasant aroma into the surrounding area and/or a sensing component to sense one or more environmental conditions, including but not limited to, motion, light, or sound and control operation of the candle based on the sensed environmental condition.

A Flameless Candle

Figure 1A:
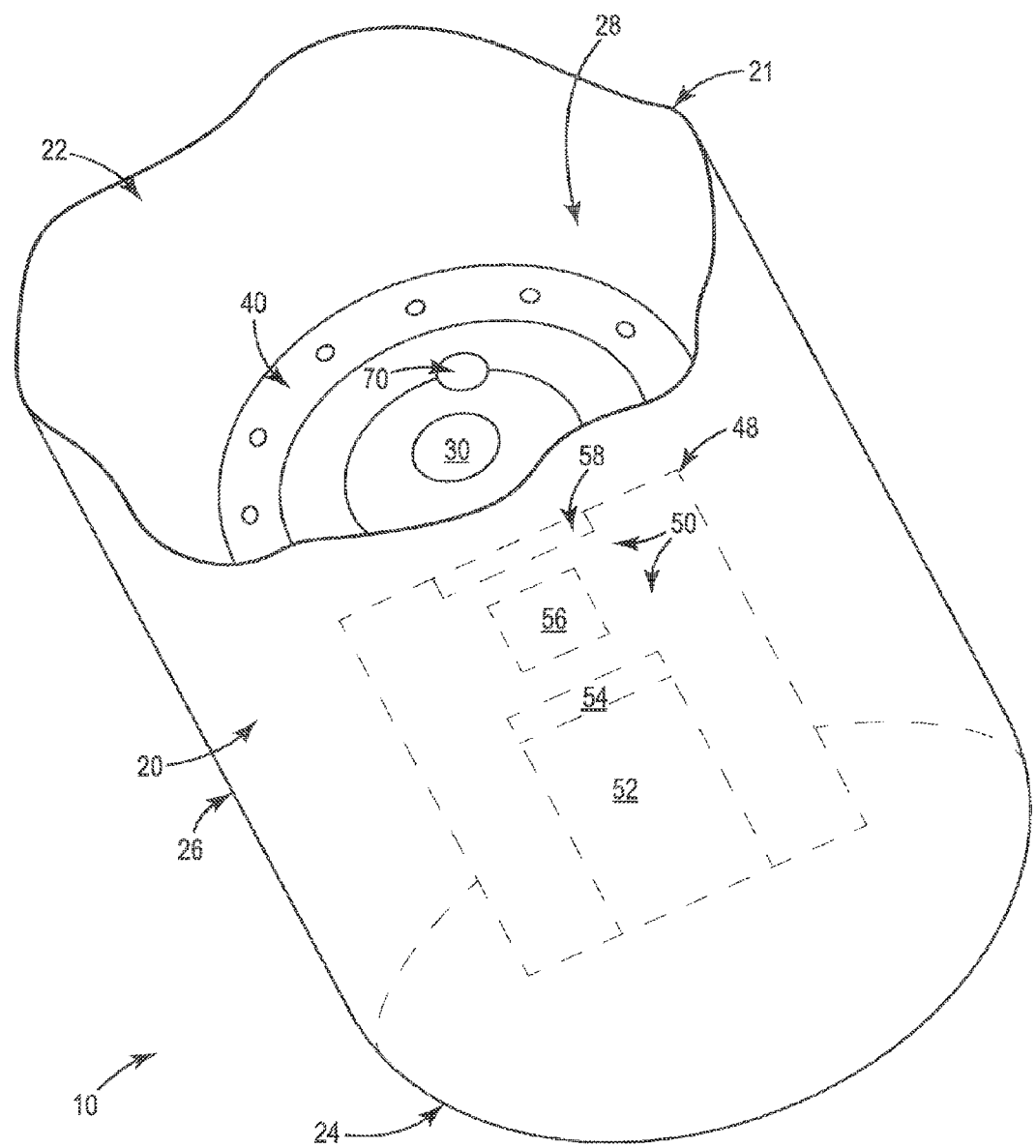
FIG. 1A is a perspective view of a flameless pillar candle, according to an embodiment of the present disclosure.

The flameless candles described herein provide a substantially more realistic flame-like light from a light source. In this regard, a flameless candle of the present disclosure may be comprised of one or more components that may function to mimic a natural flame's flicker. Referring to FIG. 1A, a flameless candle 10 may be comprised of a body 20, a control switch 30, and an electrical assembly 50. In various embodiments, the flameless candle 10 may also include a scent component 40, and a sensor component 70.

Structure

The Candle Body

Generally, as illustrated in the flameless pillar candle of FIG. 1A, the body 20 of a flameless candle 10 may be comprised of a top surface 22, a bottom surface 24 upon which the candle rests, and a sidewall 26 between the top surface 22 and the bottom surface 24. The body 20 may have desirable translucent, luminescent, and aesthetic properties to mimic the look and feel of a traditional candle. The body 20 may be made from one or more materials, including but not limited to, wax, paraffin, glass, polymeric materials, or any combination thereof.

The top surface 22 may include an indented central portion 28 to resemble a top surface of a used or partially melted traditional candle, where the wax may have been reduced by melting from the heat of the open flame in order to continue feeding the flame. In other embodiments, the central portion may not be indented. The sidewall 26 and indented central portion 28 may cooperate to create a lip 21 on the top surface 22. As seen in the embodiment of FIG. 1A, the sidewall 26 and lip 21 may cooperate to have a varied height thereby resembling the visual appearance of a used traditional candle where the wax has been reduced. The sidewall 26 may have a constant height, in other embodiments. The top surface 22 and bottom surface 24 may be circular and the sidewall 26 may extend circumferentially around the longitudinal axis, resulting in a cylindrical body 20. However, other shapes or configurations are possible and within the scope of the invention including, but not limited to, a cube, a cuboid, a cone, a pyramid, or a sphere. The bottom surface 24 may generally be flat, resulting in a stable condition of the candle when placed on a table, shelf, or other suitable flat surface. The top surface 22, bottom surface 24, and sidewall 26 cooperate to faun a cavity 48, schematically illustrated in FIG. 1A. As seen in FIG. 1B, the bottom surface 24 may also include a cover 34, that may allow easy access to the cavity 48.

Figure 1D:
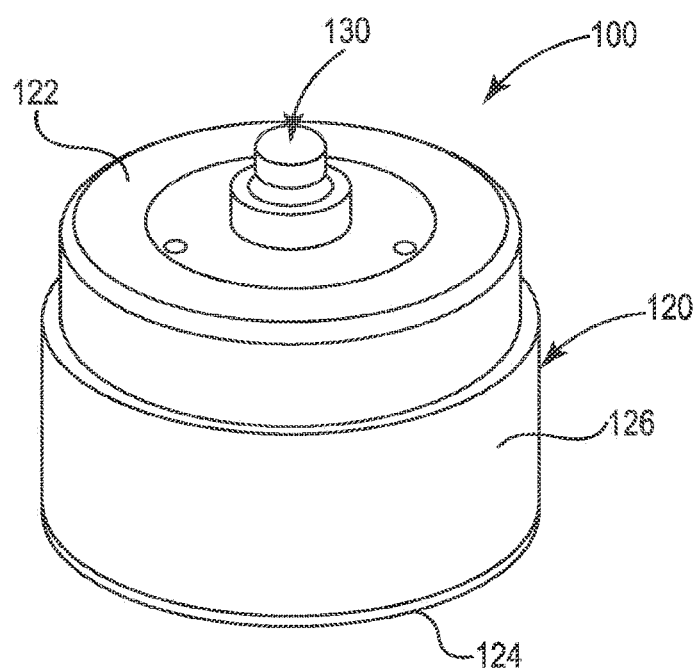
FIG. 1D is a perspective view of a flameless votive candle, according to an embodiment of the present disclosure.

Referring to FIG. 1D, the present disclosure may also be embodied in a votive flameless candle 100. The candle 100 may comprise a body 120. The body comprising a top side 122, a bottom side 124, and a sidewall 126 between the top surface 122 and bottom surface 124. Such a flameless candle 100 may generally be sized and shaped to simulate a traditional true flame votive candle, in some embodiments.

The Control Switch

Figure 3:
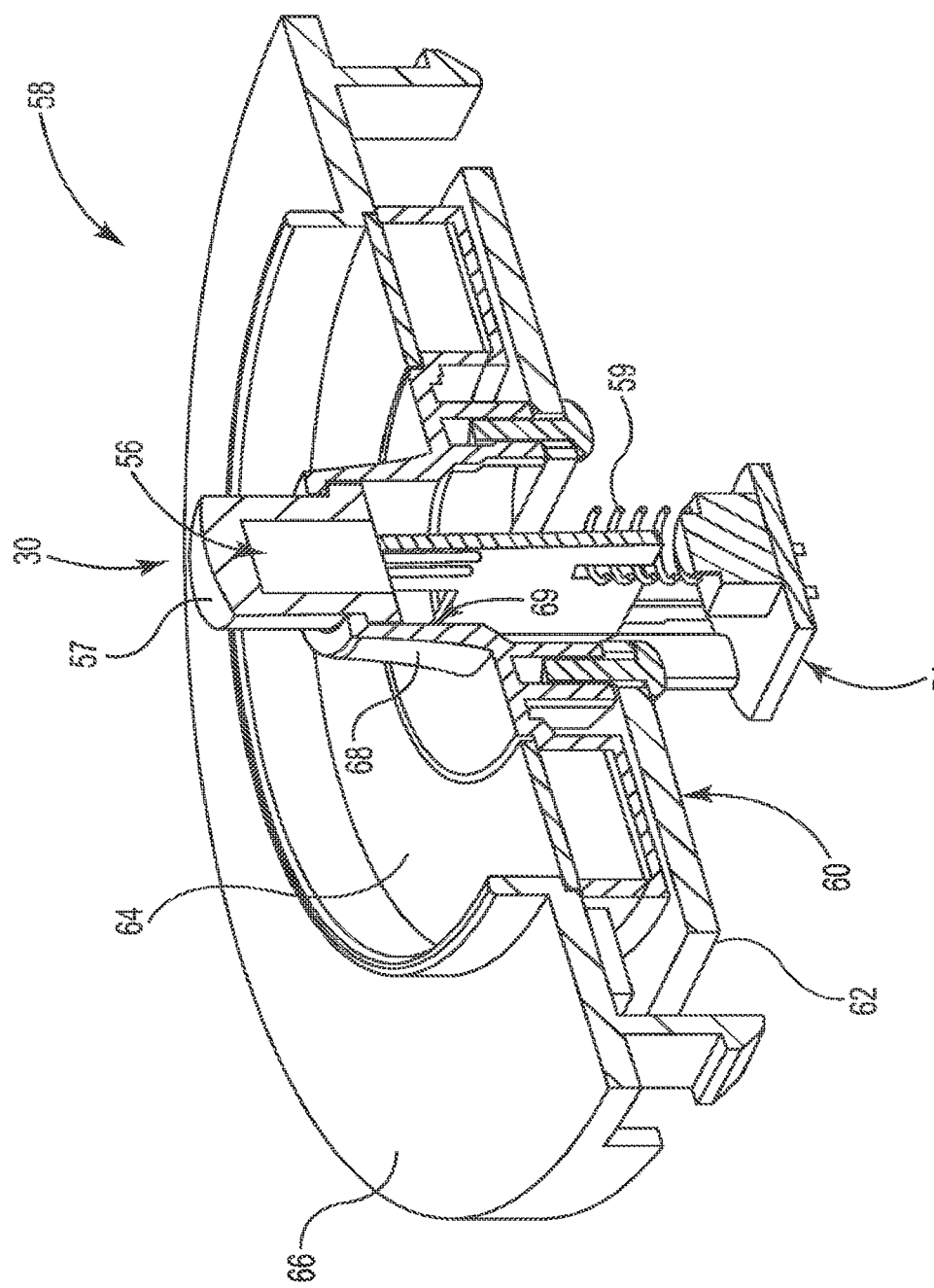
FIG. 3 is a cross-section of a control switch assembly, according to an embodiment of the present disclosure.

As illustrated in FIGS. 1A and 1C, disposed in the center of the base of the central portion 28 of top surface 22 may be an upper control switch 30. The upper control switch 30 may be a push button, toggle, slide, rotary selector switch, or any other suitable control. In alternative or additional embodiments, the bottom surface 24 may include a lower control switch 32, as seen in FIG. 1B. An upper control switch 130 may also be seen in the embodiment in FIG. 1D. By activating the control switches 30 or 130 and/or 32 separately or in conjunction, one or more functions may be activated, such as the light source 56 may begin to flicker. In at least one embodiment, the control switch 30 may house the light source 56, as seen in FIG. 3.

The Electrical Assembly

The cavity 48 may contain the electrical assembly 50, schematically illustrated in FIG. 1A. The electrical assembly may comprise one or more components, including, but not limited to, a control switch assembly 58 (shown in greater detail in FIG. 3), a power source 52, at least one circuit board 54, and a light source 56. The upper control switch 30 may be in communication with the light source 56 of the flameless candle 10. Or, as stated above, the control switch 30 may house the light source.

Control Switch Assembly

Figure 2:
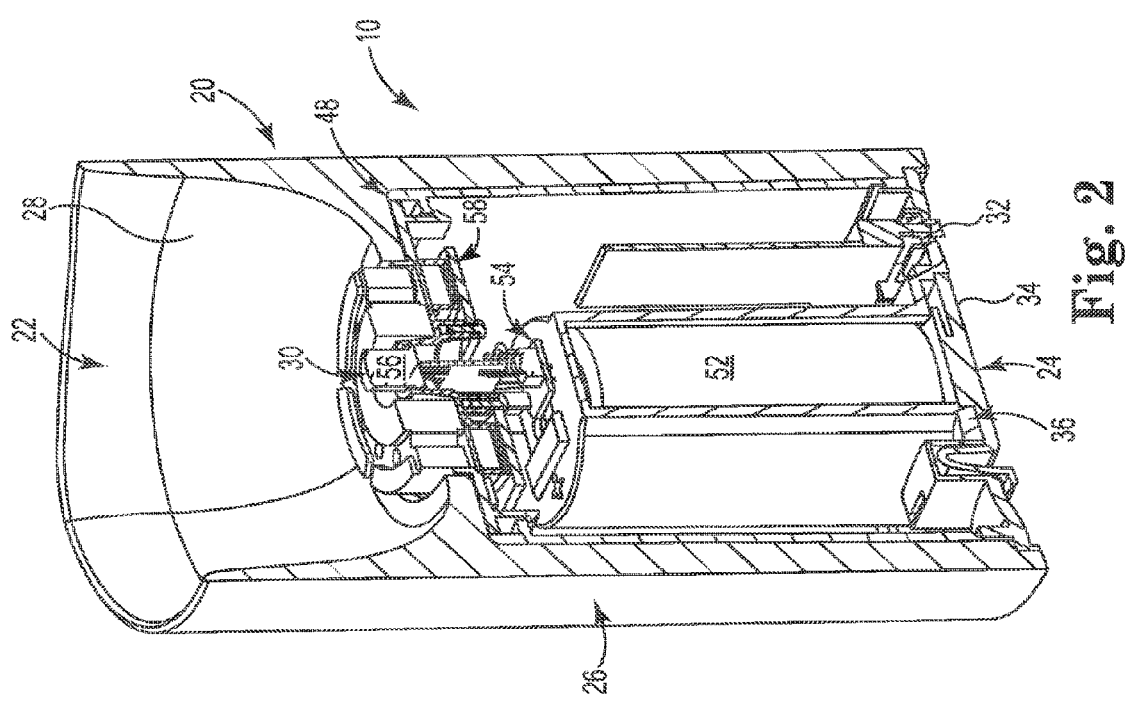
FIG. 2 is a cross-section of a flameless pillar candle, according to an embodiment of the present disclosure.

Referring to FIG. 2, the control switch assembly 58 may retain the control switch 30. The control switch assembly 58 may be comprised of one or more components. In one embodiment as seen in FIG. 3, the control switch assembly 58 components may include, but are not limited to, a push button control switch 30, a spring 59, and a retaining assembly 60. The spring 59 may be disposed between the light source 56 and the circuit board 54. In other embodiments, the light source may be positioned below the spring and the circuit board. The light source 56 may be brought into electrical and mechanical communication with the circuit board 54. For example, a push button control switch 30 may be pressed down so that it is in an "on" position resulting in the spring 59 compressing. The light source 56 may become electrically engaged with the circuit board 54. When the push button for the control switch is pressed down again, the spring 59 may release and the push button returns to an "off" position. In at least one such embodiment, when the spring 59 is released, the light source 56 is electrically disengaged from the circuit board 54. In other embodiments, for example those not using a push button, a spring may not be present.

The control switch assembly 58 may further comprise a retaining assembly 60. The retaining assembly 60 may have a circumferential outer conical portion 68 that mates with a circular opening within the top surface of the candle body. In at least one embodiment, the retaining assembly 60 may have a central lumen 69 through which the control switch 30 may be able to slide. In at least one embodiment, when installed within the top surface, the retaining assembly 60 is flush with the surrounding surface of the indented central portion 28 of the body 20. The retaining assembly 60 may comprise several components that are assembled to hold the control switch assembly 58 within the candle body. The components may, in some embodiments, comprise a plurality of concentric mating rings, each with a different inner and out diameter. In the embodiment of FIG. 3, there may be an inferior ring 62, a superior inner ring 64, and a superior outer ring 66. In various embodiments, the circumferential outer conical portion 68 may be comprised within the superior inner ring 64. While the retaining assembly 60 described and shown herein comprises a plurality of concentric mating rings, other shapes or configurations are possible and are within the scope of the invention. Such other shapes or configurations include but are not limited to cubes, rectangular solids, cones, pyramids, spheroids, and irregular shapes. In some embodiments, the retaining assembly components are integrally formed. In some embodiments, the retaining assembly is made from a wax, paraffin, glass, polymeric materials, or combinations thereof. In some embodiments, the configuration of the retaining assembly 60 and the selected material may have desirable translucent, luminescent and aesthetic properties to mimic the look and feel of a traditional candle.

Power Source

Referring back to FIG. 2, the power source may provide power to the electrical assembly, resulting in the light source being illuminated. The power source 52 may be disposed within a power source compartment 36. As shown in the embodiment of FIG. 2, the power source 52 may comprise one or more batteries. The power source 52 may be adjacent to the cover 34 and centrally located, allowing an ease of access to change the battery. In other embodiments, the power compartment may be located proximal to the sidewall 26, superior to the rest of the electrical assembly, or exterior to the flameless candle 10. The power compartment may be located in any suitable location. The power source may be one or more standard alkaline batteries, one or more rechargeable batteries, a USB charged power source, a power cord, a power source charged by induction charging, any other suitable source, or any combination thereof.

Light Source

The light source may illuminate the flameless candle. The light source may be a LED that comprises one or more diodes, in various embodiments. The light source may be an incandescent lamp, in other embodiments. The light source may be a gas discharge lamp, in yet another embodiment. It should be understood that any suitable light source may be used. The light source may preferably be located on a midline of the body 20 of the candle in order to mimic traditional candles, as seen in FIG. 2. In other embodiments, the light source may be located more proximal to the sidewall. In at least one embodiment, the light source may be located superior to the transverse plane, or in the top half of the candle. However, a light source located at any point within the body of the candle is within the scope of the present disclosure.

Referring to FIG. 3, the light source 56 may be built into a customized housing 57, in some embodiments. The customized housing 57, in one embodiment, has a concave top surface, but in other embodiments can be convex or may be a flat top surface. The customized housing 57 may also have a concave bottom surface, convex bottom surface, or flat surface. In some embodiments, the customized housing 57 may be made of a clear, translucent or opaque material. In at least one embodiment, the customized housing may be coated with a plurality of specks of an orange or yellow coating arranged in a specific pattern to make the light appear more natural. In at least one embodiment, as shown in FIG. 3, the light source 56 and the customized housing 57 may form a push button of the control switch 30.

In some embodiments, the light source may be comprised of one or more lights, or one or more LED diodes. In various embodiments, different colored lights may be used to better mimic the color of a flame. For example, in one embodiment, the light source may by a combination of red, yellow, orange, and/or white LEDs. The lights may cooperate to mimic the colors of a natural flame.

Circuit Board

Figure 4:
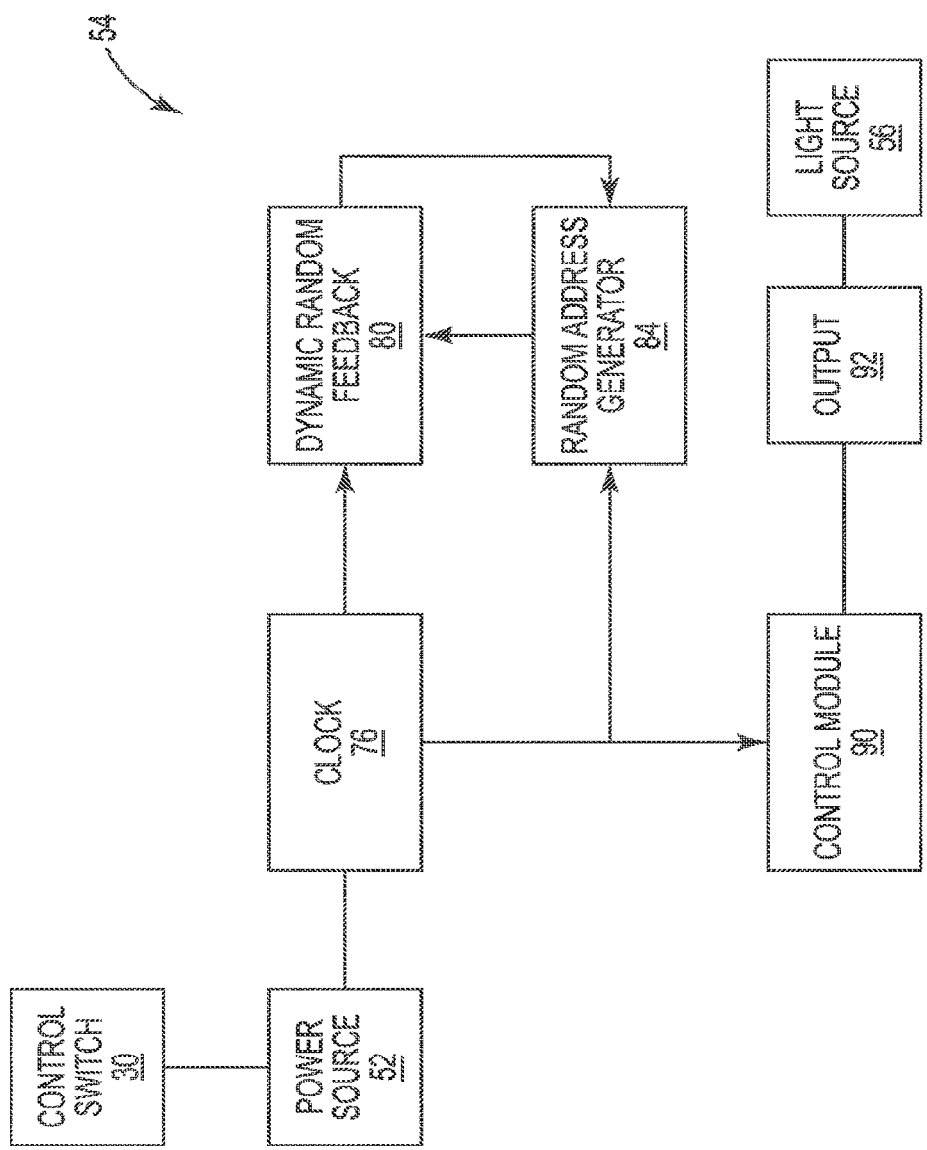
FIG. 4 is a schematic of a circuit board, according to an embodiment of the present disclosure.

As seen in the example of FIG. 4, a circuit board 54 may be in electrical communication with the power source 52, the light source 56, and any control switch 30, 32. The circuit board may be comprised of one or more components. In one embodiment, the circuit board components may include, but are not limited to, a clock 76, an analog-to-digital converter 80, a random address generator 84, a random sequence generator 90, and an output 92. The output 92 may be in communication with the light source 56. The functionality of the circuit board 54 is discussed below.

Function

The upper control switch 30 and/or lower control switch 32, herein called the control switch, may be in communication with a light source (or light) 56. The control switch may be a push button, toggle switch, slide switch, or any other suitable component. The control switch may be configured to, when selected by the user, modify the frequency of a light's flicker, the luminescence of the light, the color of the light, or the timer settings of the light. In at least one embodiment, the control switch may be a push button, which when depressed selects a particular mode of the candle. In one embodiment, the modes include, but are not limited to, a flicker mode, a static light mode, and an off mode. For example, depressing the push button of the control switch may activate the light source in flicker mode. A light in flicker mode may randomly dim and brighten in such a way that mimics a flame from a traditional candle. Depressing the push button a second time may activate the light source in static mode. A light in static mode may be on but may not flicker. Depressing the push button a third time may activate a timer mode. A light in timer mode may automatically turn off after a set time period. Depressing the push button a fourth time may deactivate the light, or result in an off mode. Any suitable means of activation or deactivation of any mode may be used.

In some embodiments, the candle may produce an indication of the mode selected. It at least one embodiment, when the user depresses the control switch, the light source may flash any number of times to indicate a certain mode has been selected.

Flicker Mode

The natural flicker may be controlled by one or more methods, including, but not limited to a random signal method.

A random signal method may generate one or more random signals resulting in a natural "flicker" from the light source. As noted above, FIG. 4 is an electrical schematic for one embodiment of the circuit board 54 of the present disclosure. Clock 76 may be in electrical communication with the power source 52. When the power source 52 is activated by control switch 30, clock 76 may provide an input signal to at least the random address generator 84. The random address generator 84 may provide a random signal to the dynamic random feedback 80. The dynamic random feedback 80 may be or may comprise an analog-to-digital converter, in some embodiments. The random signal may vary in one or more aspects including, but not limited to, amplitude, frequency, and duty cycle. The duty cycle may be the period of time it takes for a signal to complete an on-and-off cycle. In at least one embodiment, the random address generator 84 may use pulse-width modulation to modify the signal, which results in controlling the power supplied to the light source. Pulse-width modulation may be used to manipulate (increase or decrease) the power a light source receives at very high rates. This manipulation may result in a perceived flicker as the light source is quickly changed from high luminescence to low luminesce and back again.

The dynamic random feedback 80 may convert the random signal to a digital signal which is then transmitted to the control module 90. The control module may be or may comprise a random sequence generator, in some embodiments. The control module may control one or more light source aspects, including but not limited to light brightness and time. The control module 90 may manipulate the random signal received from the dynamic random feedback 80 into a second random signal; although such is not required. The second random signal may also vary in one or more aspects to control the brightness and duration in the light source. In one embodiment, the second random signal variations may include, but are not limited to, amplitude, frequency, and duty cycle. In at least one embodiment, the control module 90 may also use pulse-width modulation to modify the signal. The second random signal from the control module 90 may be output via output 92 to the light source 56.

Figure 5:
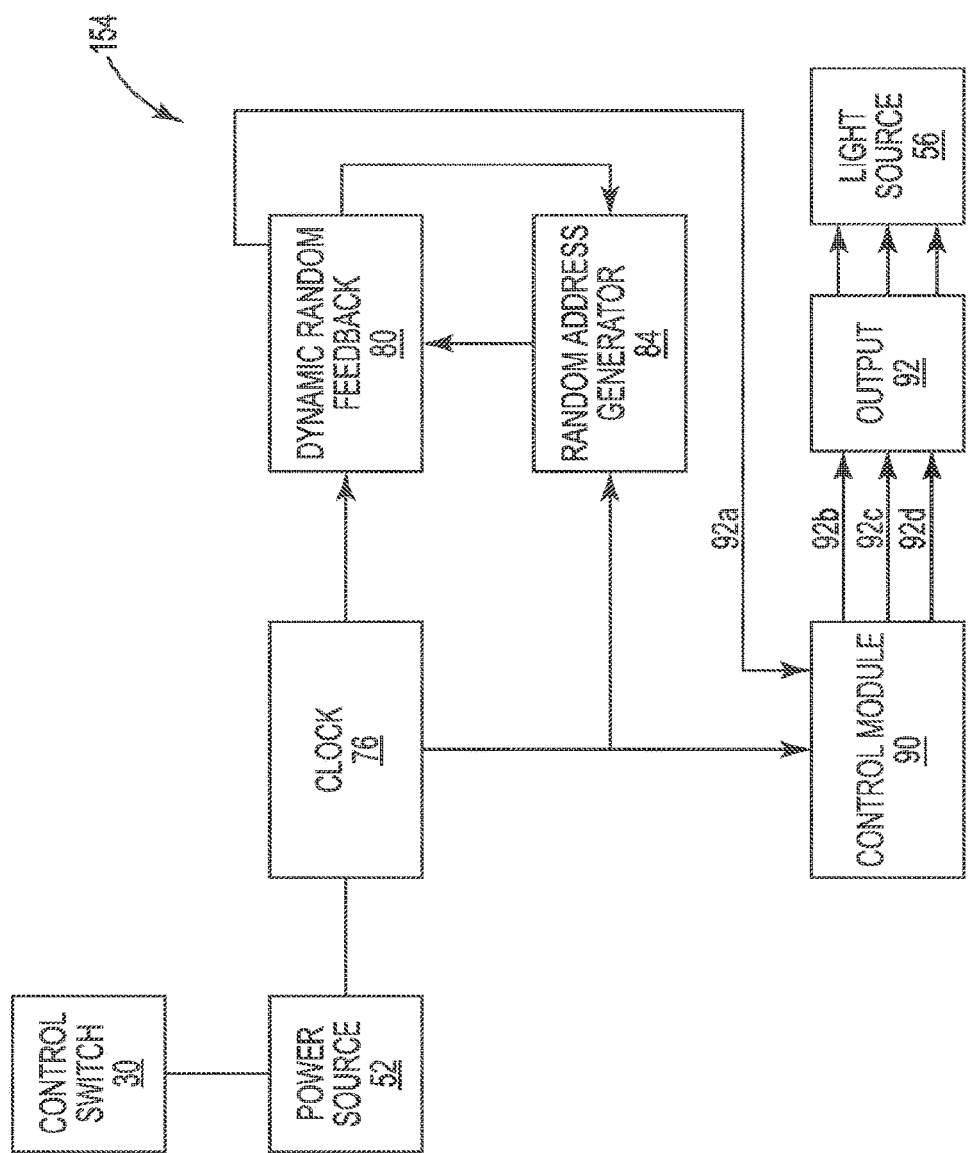
FIG. 5 is a schematic of a circuit board, according to an embodiment of the present disclosure.

In one embodiment, using LED light diodes, the second random signal may be output to one or more diodes. As illustrated in FIG. 5 the control module 90 may convert the random signal 92a into one or more random signals 92b, 92c, and 92d each being output to a separate diode via output 92. The signal transmitted randomly to one or more of the diodes of the LED 56 may produce a natural "flicker" of light to the human eye.

The natural "flicker" may have a 72-hour cycle, in some embodiments. A 72-hour cycle may provide an optimal battery life, in some embodiments, where a battery is used as the power source. For example, a random, or seemingly random pattern may be used for a 72-hour cycle, at the end of which the random pattern may then repeat. In some embodiments, a 24-hour cycle may be used. In other embodiments, a 48-hour cycle may be used. It should be understood that a cycle of any duration may be used.

Static Mode

A light source in static mode may be on, and may not flicker. In various embodiments, the static mode may be set to varying degrees of luminosity. That is, the light source may be dimmed to one or more levels. The power supply 52, may supply power directly to the light source 56, in some embodiments. In other embodiments, the power supply may pass through the clock 76 before reaching the light source 56, thereby allowing a timer mode to be activated.

Timer Mode

The flameless candle may have a timer, where the light remains on for a predetermined timed period. In some embodiments, the timed period may be automatically set. For example, activation of the timer may keep the light source on for one hour and then turn the candle off. In other embodiments, the user may set the timer to any desired time. In one embodiment, the user may select the timer by depressing a control button until the timer mode is selected. In one example, the light source may flash three times to indicate the timer mode has been selected. The user may then push the control switch any number of desired times, each depression of the control switch adding a predetermined period of time. In other embodiments, there may be a USB port that a user may plug into the candle with preloaded timer settings. In still another, there may be a separate control switch for the timer mode, or two or more control switches may, together, activate the timer mode. Any suitable method to set a timer for the candle may be used.

Scented Flameless Candle

A flameless candle of the present disclosure may additionally or alternatively have a scented component that may provide a scent or aroma to the surrounding environment. In some embodiments, the scented component may be a scented cartridge. The scent may be diffused through the cartridge and into the surrounding environment when heat or an electric current is applied to the scent cartridge, in some embodiments.

Figure 6:
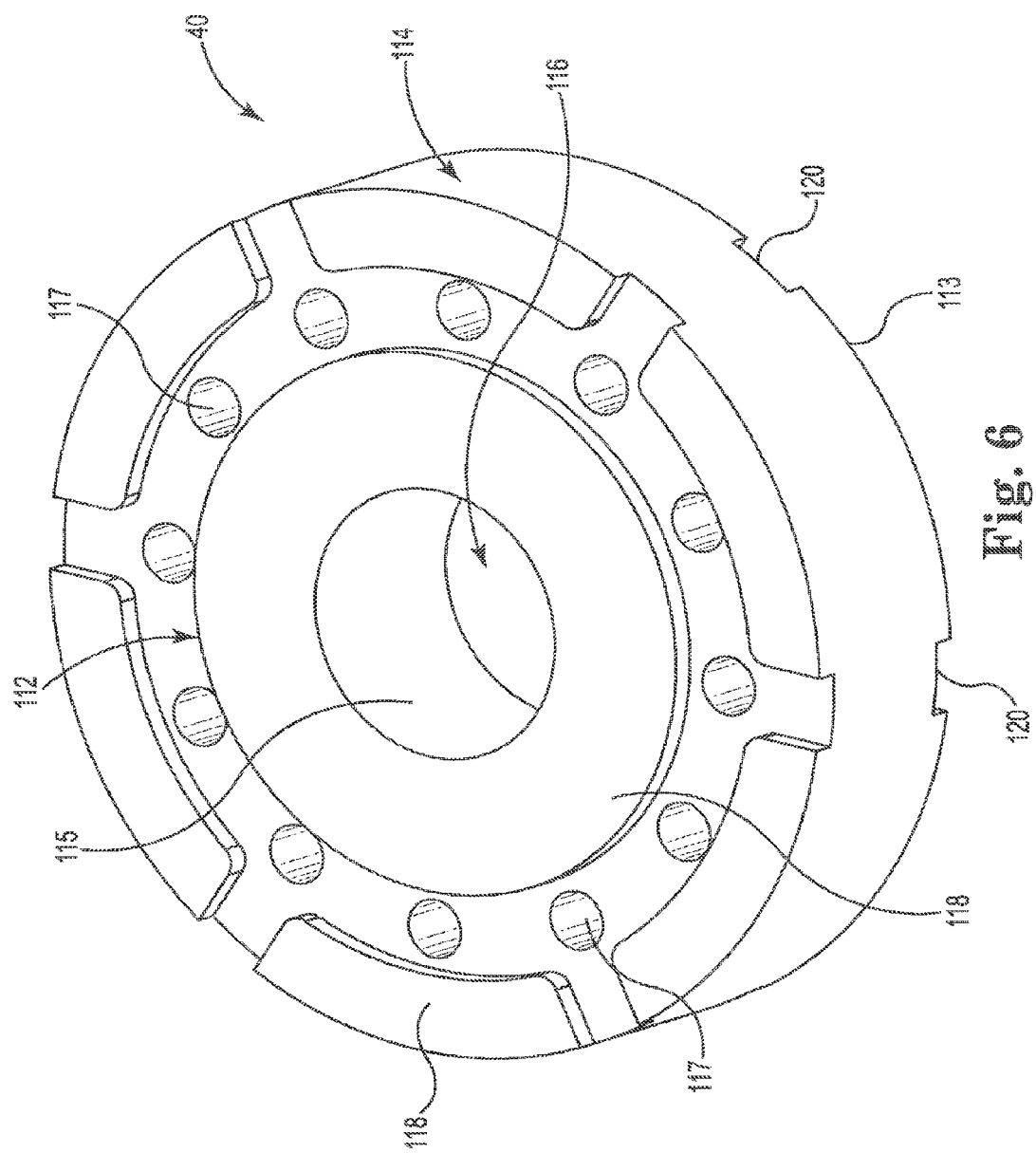
FIG. 6 is a perspective view of a scent cartridge, according to an embodiment of the present disclosure.

Referring to FIG. 6, a scent cartridge 40, may be comprised of a top surface 112, a bottom surface 113, and an outer sidewall 114 that extends between the bottom surface 113 and the top surface 112. In some embodiments, the scent cartridge 40 may further comprise an inner sidewall 115, extending between the bottom surface 113 and the top surface 112, thereby defining a hole 116. The top surface 112, bottom surface 113, and sidewalls 114, 115 may cooperate to define a chamber, or cavity 119 (seen in FIG. 7). The cavity 119 may contain one or more fragrance impregnated materials. In one embodiment, the fragrance impregnated material may be a fragrant liquid. In another embodiment, the fragrance impregnated material may be a fragrant disk. Any suitable fragrant material may be used.

The top surface may comprise one or more openings 117 through which a fragrance vapor, or scent, may be diffused. The openings 117 may have a diameter that is between five and ten percent of the outer diameter of the scent cartridge 40, in various embodiments. In some embodiments, the openings 117 have a diameter between about two millimeters and twenty millimeters. In other embodiments, the openings may have any suitable diameter. It should also be understood the openings 117 may be circular holes, slats, or any other suitable opening for diffusing the scent. The openings 117 may have a depth that is less than the height of the outer sidewall 114, in some embodiments. In other embodiments, the openings may have a depth equal to the height of the outer sidewall 114. In still other embodiments, there may be openings 117 on the surface of inner sidewall 115 or outer sidewall 114. The top surface 112 may comprise a plurality of surface features 118. Surface features 118 may include, but are not limited to, bumps, ridges, protrusions, channels, and reliefs. Surface features 118 may further assist with diffusing the scent.

The bottom surface 113 of the scent cartridge 40 may be flat, in some embodiments. In other embodiments, the bottom surface 113 may have surface features 120 that allow the bottom surface to rest properly without shifting within the flameless candle 10. In at least one embodiment, the bottom surface 113 has a plurality of surface features 120 that engage with surface features on the indented central portion 28 of the flameless candle 10. By rotating the scent cartridge 40, the surface features on the bottom surface 113 may substantially align and/or lock with the surface features on the flameless candle 10 to hold the scented cartridge 110 in place. In some embodiments, the top surface 112 may have the same configuration of surface features 120 as the bottom surface 113 allowing the scent cartridge 40 to be flipped or turned over for prolonged use.

The light source, as discussed above, may be disposed inside the body of the candle, within the control switch assembly, or in any other suitable position. In at least one embodiment, the light source may be disposed within a central portion of the scent cartridge, allowing the user to replace the light and the scent simultaneously.

Figure 7:
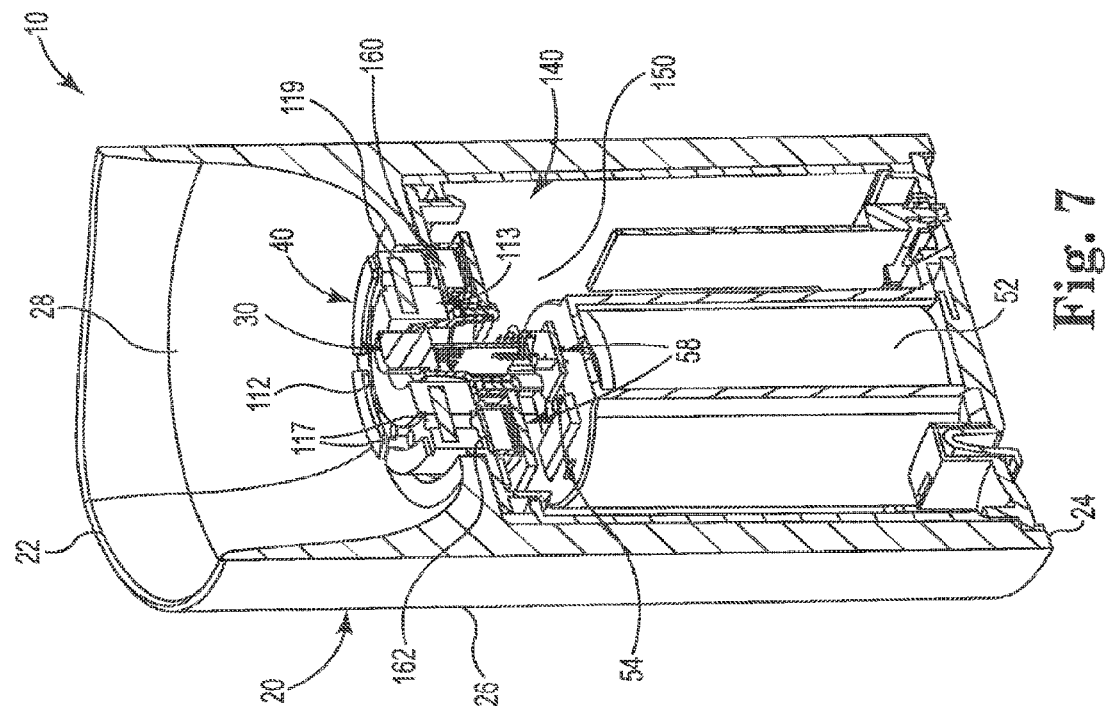
FIG. 7 is a cross-section of a flameless pillar candle, according to an embodiment of the present disclosure.

Referring to FIG. 7, a scent cartridge 40 may be disposed within the indented central portion 28 of flameless candle 10. In at least one embodiment, the bottom surface 113 of the scent cartridge 40 may be flush with the base of the indented central portion 28. In other embodiments, as seen in FIG. 7, the hole 116 may be positioned over a control switch 30, the control switch 30 at least partially extending outwardly from the scented cartridge 40. In still other embodiments, the scented cartridge may be positioned to act on the control switch. For example, the scented cartridge which may, for example, have no hole 116, may be placed in the indented central portion 28. A user may be able to push onto the scented cartridge, which may in-turn push onto a push button control switch, thereby depressing the control switch.

In still other embodiments, a control switch may be integrated into the scent cartridge.

Activation of a control switch may, in addition to activating a light source, turn on or off a heating element or otherwise activate the scent mode of the candle. To provide heat to the scent cartridge 40, the flameless candle 10 may further comprise a heating element 160, which may be in direct contact with, in nearly direct contact with, adjacent to, or otherwise close to the scent cartridge 40. However, any suitable position allowing the heating element 160 to heat the scent cartridge 40 may be used. The heating element 160 may also be in communication with the circuit board 54. In at least one embodiment, the heating element 160 may be situated between the control switch assembly 58 and the scent cartridge 40. In one embodiment, the heating element 160 may have an outer surface 162 that cooperates, or mates, with the bottom surface 113 of the scent cartridge 40, in order to apply direct heat. When a user selects to activate the heating element 160, heat may be applied to the bottom surface 113 of the scent cartridge 40, resulting in an emission or diffusion, of the fragrant scent.

Figure 8:
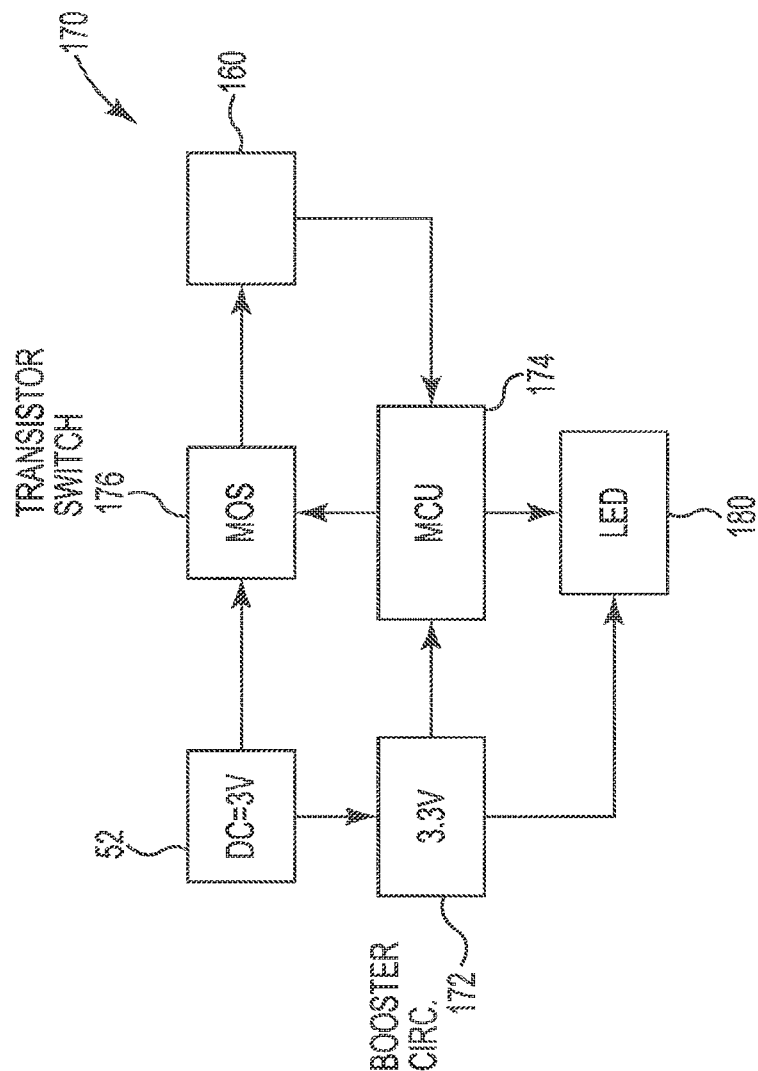
FIG. 8 is a schematic of a circuit board with a heating element, according to an embodiment of the present disclosure.

FIG. 8 illustrates an example circuit schematic for the circuit board in an embodiment involving a heating element. The circuit 170 may comprise a power source 52, a booster circuit 172, an MCU detection circuit 174, a transistor switch 176, and the heating element 160. In some embodiments, the circuit may also include a light source circuit 180. The light source circuit may, in some embodiments, be a circuit such as that illustrated by FIG. 4, discussed above. The light source circuit and heating element circuit may share some or all common components. The power source 52 may provide a voltage to the MCU detection circuit 174 through the booster circuit 172, in some embodiments. In other embodiments, the power source 52 may provide a voltage directly to the MCU detection circuit. The booster circuit 172 may amplify the voltage obtained from the power source 52 and provide it to the MCU detection circuit 174. In various embodiments, the booster circuit 172 may provide an amplified voltage to the light source circuit 180. The MCU detection circuit 174 may output high and low electric levels to control the transistor switch 176. The transistor switch 176 may connect the MCU detection circuit 174 with the heating element 160, thereby affecting one or more heating element modes as well as the temperature of the heating element 160. Heating element modes may include, but are not limited to, on, on-high, on-low, off, or timer.

In various embodiments, based on one or more control switch 30, 32 inputs, the MCU detection circuit 174 may output various high and low electric levels over a desired time period, herein referred to as high-low cycle. The high-low cycle may enable a cyclic on and off interval of heating by turning the transistor switch 176 on and off based on the electric levels. For example, a user may select a scent feature mode having a duration of four hours. The MCU detection circuit 174 may output a high-low cycle resulting in the transistor switch 176 turning the heating element 160 on for thirty minutes, off for two hours, on for ten minutes, off for thirty minutes, on for ten minutes, off for thirty minutes, and then off. In such an embodiment, when the control switch 30, 32 is pressed again, the cycle may be cancelled and the light source 30 may turn off.

The MCU detection circuit 174 may incorporate a temperature sensor 182, as shown in the detailed circuit schematic example of FIG. 9. By converting the temperature change of the heating plate to a voltage change, the temperature of the heating plate can be tested and controlled by the MCU detection circuit 174. When the temperature is equal to or greater than a desired value, the MCU detection circuit 174 may turn the transistor switch 176 off, resulting in cutting off power to the heating element 160. The desired high temperature value may be, at least in part, dependent upon at least the material properties of the scent cartridge 40. In at least one embodiment, the desired high temperature value may be about fifty degrees Celsius (one-hundred and twenty two degrees Fahrenheit). In general, the desired high temperature value can be between about forty-five degrees Celsius (about one-hundred and thirteen degrees Fahrenheit) and fifty-five degrees Celsius (about one-hundred and thirty one degrees Fahrenheit). When the temperature is equal to or lower than a desired value, the MCU detection circuit 174 may turn the transistor switch 176 on, sending power to the heating element 160, and thereby turning the heating element 160 on. In at least one embodiment, the desired low temperature value may be about five degrees Celsius lower than the desired high temperature value. The desired low temperature value may be, at least in part, dependent upon the material properties of the scent cartridge 40. In at least one embodiment, the desired low temperature value is about forty-five degrees Celsius (about one-hundred degrees Fahrenheit). In general, the desired low temperature value can be between about thirty-eight degrees Celsius (about one-hundred degrees Fahrenheit) and fifty degrees Celsius (about one-hundred and twenty-two degrees Fahrenheit). However, it should be understood that any suitable temperature (s) to heat the heating element 160 may be used and are within the scope of the present disclosure.

Sensing Flameless Candle

A flameless candle of the present disclosure may additionally or alternatively have a sensing component, in various embodiments. In some embodiments, the sensing component may be a motion sensor that may allow a user to use hand motions, or other motions, to select various functions, or modes, of the flameless candle. The modes may include, but are not limited to, whether the light is on or off, whether the light is in a static mode or flicker mode, the duration the light is on, the color of the light, the luminescence of the light, and whether a scent mode is on. In other embodiments, the sensing component may be an optical sensor that may allow one or more modes to be selected based on the ambient light in the surrounding environment. For example, when the ambient light is reduced, such as at dusk, the optical sensor may detect the change and turn the flameless candle's light on. In still other embodiments, the sensing component may be an audio sensor that may allow the user to use audio cues to select various functions, or modes, of the flameless candle. In one embodiment, the sensing component may be able to detect air movement, allowing a user to select a various mode, such as turning the flameless candle off, by blowing on the sensor, simulating a method of blowing out a traditional true flame candle. In some embodiments, the sensing component may be a Bluetooth, radio, or other wireless component able to receive a wireless signal from a computer, remote, handheld device, or any other suitable device. For example, a user may select a flicker mode on a timer for two hours from her handheld device. The device may transmit a signal that may be received by the sensing component in the wireless candle, resulting in the candle being configured to remain in flicker mode for two hours and then turn off. One or more sensors may be used in various embodiments of the present disclosure.

Figure 9A:
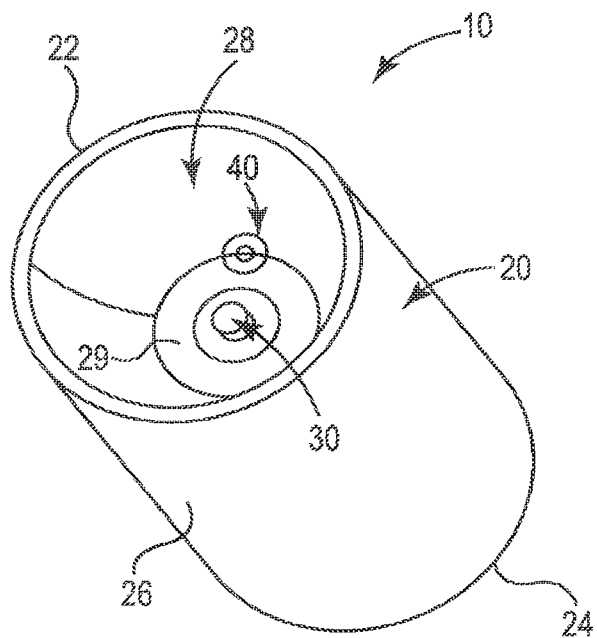
FIG. 9A is a perspective view of a flameless candle with a sensor, according to an embodiment of the present disclosure.
Figure 9B:
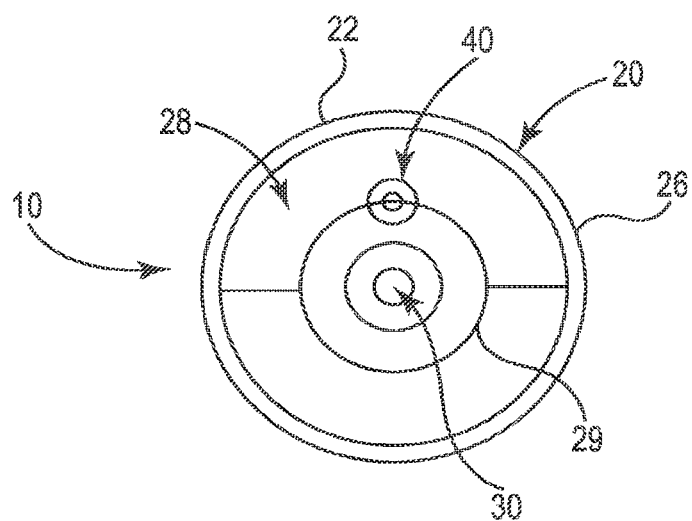
FIG. 9B is a top view of a flameless candle with a sensor, according to an embodiment of the present disclosure.

A flameless candle may comprise a motion sensor, in various embodiments. As seen in FIGS. 9A-9B a motion sensor 70 may be disposed within the indented central portion 28. In some embodiments, the motion sensor 70 may be radially offset from the center of the base 29 of the central portion 28. In various embodiments where a scent cartridge may be used, the motion sensor 70 may be spaced sufficiently away from the center of the base 29 so as not to be covered by the scent cartridge. In some embodiments, the motion sensor 70 may be integrated with the upper control switch 30. In at least one embodiment the motion sensor 70, upper control switch 30, and light source may be integrated. In other embodiments as seen in FIG. 10, the motion sensor 70 may be embedded within the body 20 of the flameless candle 10. By embedding the motion sensor 70 into the body 20 of the flameless candle 10, the candle may have additional functionality while being aesthetically similar to a traditional candle. Any suitable location to embed the motion sensor 70 may be used and is within the scope of the present disclosure.

A motion sensor assembly may house the motion sensor. Similar to the control switch assembly discussed above, the motion sensor assembly may be in communication with the power source, the light source, and a circuit board. Referring additionally to the exploded view in FIG. 11, when installed within the cavity 49, the motion sensor assembly 61 may be flush with the surrounding surface of the body 20 and/or may be flush with the indented central portion on the top surface 22. In some embodiments, the motion sensor assembly 61 is made from a wax, paraffin, glass, polymeric materials, or combinations thereof. In some embodiments, the configuration of the motion sensor assembly and the selected material may have desirable translucent, luminescent and aesthetic properties to mimic the look and feel of a traditional candle.

The motion sensor may emit electromagnetic waves. By using different hand motions, electromagnetic induction modules may produce different waveform outputs to perform different product function statuses (such as on or off). By activating the motion sensor 70, the light source 56 of the candle may be illuminated, in various embodiments. In at least one embodiment, a control switch may activate the power supply before the motion sensor may change the mode.

Figure 12:
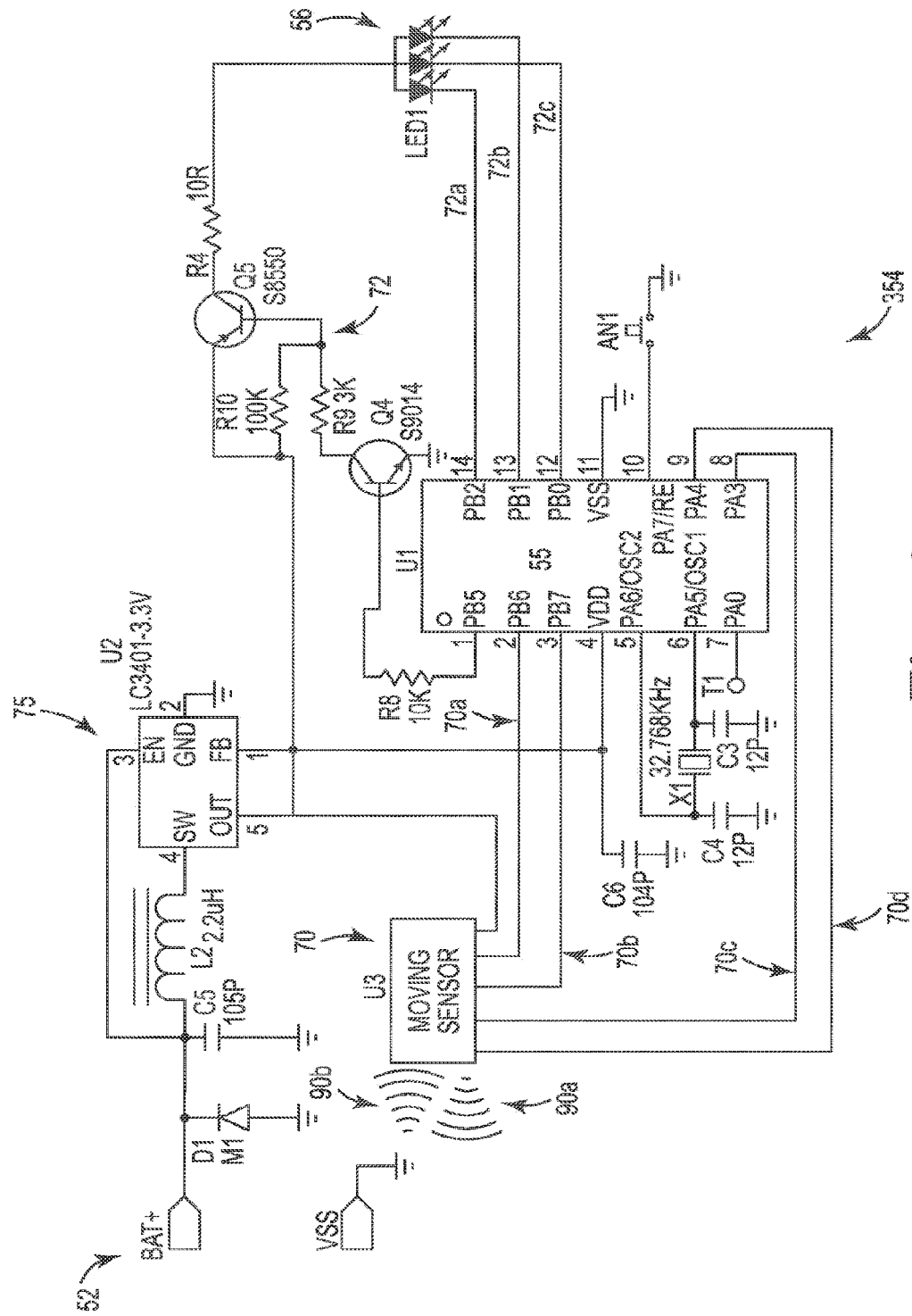
FIG. 12 is a schematic of a circuit board with a motion sensor, according to an embodiment of the present disclosure.

Referring additionally to FIG. 12, which is an electrical schematic for one embodiment involving a motion sensor, as power is supplied from the power source 52 optionally through a booster circuit 75 to the motion sensor 70, the motion sensor 70 may emit electromagnetic waves 90*a*. Based on different motions at a certain distance, the electromagnetic waves may be reflected and the motion sensor 70 may receive the different electromagnetic waves 90*b*. Through the internal processing of the motion sensor 70, the motion sensor 70 may output one or more signals 70*a*, 70*b*, 70*c*, and 70*d* to the control circuit 55, which may be connected to the light source 56. Based on the signal(s) 70*a*, 70*b*, 70*c*, and 70*d* received from the motion sensor 70, the control circuit 55 may adjust, among other features, the brightness or color of the light, the emission of scent, turn the light source 56 on or off, adjust any other mode or function, or perform any combination thereof.

In one particular embodiment, the light source 56 may be off and the candle may be in a standby mode. When the power source 52 is turned on, at least one oscillator of the control circuit 55 may output a high level voltage continuously to a transistor circuit 72 of the circuit board 354. This high level voltage may be continuously supplied to a first transistor of the transistor circuit 72 until it reaches a saturation conduction. The voltage may then pass through to a second transistor of the transistor circuit 72, whereby the second transistor is conducted. The voltage may then pass to the light source 56, in essence turning the light source on. The voltage may then pass back to the control circuit 55 as three outputs 72A, 72B, and 72C. The three outputs 72A, 72B, and 72C may form square wave outputs, thereby affecting the amplitude of the voltage provided to the light source, which may cause the light source 56 to flash. In some embodiments, the control circuit 55 may utilize pulse modulation to control brightness of the light source 56.

Figure 13:
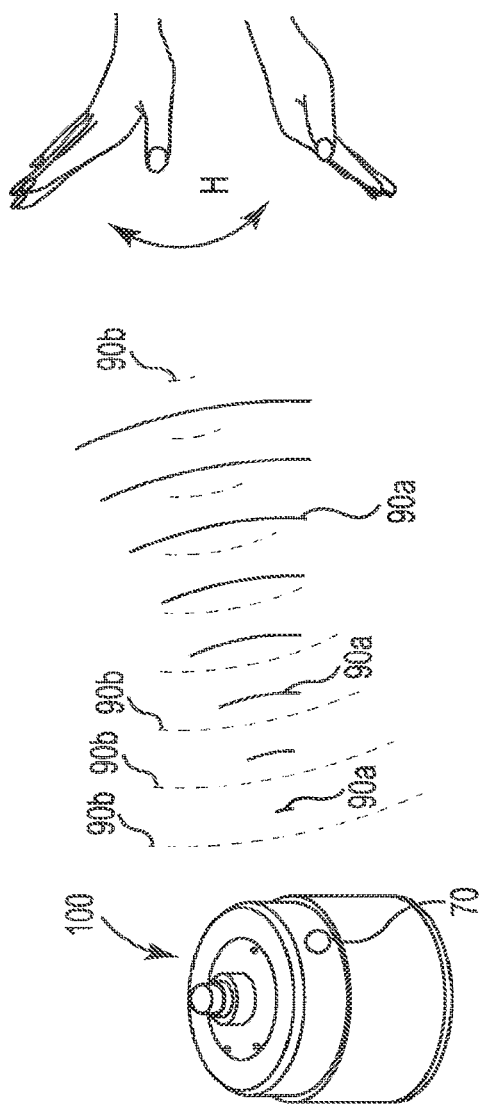
FIG. 13 illustrates how a motion sensor functions with a flameless votive candle, according to an embodiment of the present disclosure.

FIGS. 10 and 13 illustrate different embodiments of a flameless candle with the motion sensor in use. The motion sensor 70 may emit a plurality of electromagnetic waves 90a that proceed unimpeded until a user's hand H makes a gesture, motion, or movement. The movement may reflect the electromagnetic waves 90b back to the motion sensor 70. As discussed above, through the internal processing of the motion sensor 70, the motion sensor converts the reflected electromagnetic waves 90b into output signals that are processed by a control circuit of the candle. The motion sensor 70 may have a working range of about five meters (about seventeen feet). In other embodiments, the motion sensor 70 may have a working range of ten meters (about thirty-three feet). In one embodiment, the motion sensor may have a range of over ten meters. The motion sensor 70 may have any desired working range in various embodiments of the present disclosure.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

I claim:

1. A removable fragrance cartridge for use in an imitation candle device, the removable fragrance cartridge comprising:
   a top surface including one or more holes to provide one or more pathways for diffusion of a fragrance from an interior of the fragrance cartridge to an area outside of the fragrance cartridge, the top surface including a plurality of surface features to further assist with diffusion of the fragrance;
   a bottom surface;
   an outer sidewall extending between the top surface and the bottom surface;
   an opening in the top surface defined by an inner sidewall extending between the top surface and the bottom surface, the opening formed at a central location of the fragrance cartridge such that, upon placement into the imitation candle device, the opening is positioned below an illuminated element protruding from a top section of the imitation candle device; and
   a chamber defined by the top surface, the bottom surface, the inner sidewall, and the outer sidewall, wherein the chamber comprises one or more fragrance materials.

2. The removable fragrance cartridge of claim 1, wherein the one or more holes are shaped as a circular opening.

3. The removable fragrance cartridge of claim 1, wherein the one or more holes have a diameter that is between five and ten percent of the outer diameter of the fragrance cartridge.

4. The removable fragrance cartridge of claim 1, wherein the one or more holes have a diameter between about two millimeters and twenty millimeters.

5. The removable fragrance cartridge of claim 1, further comprising one or more holes in the inner sidewall between the top surface and the bottom surface.

6. The removable fragrance cartridge of claim 1, further comprising one or more holes in the outer sidewall between the top surface and the bottom surface.

7. The removable fragrance cartridge of claim 1, wherein the opening extends through both the top and bottom surfaces.

8. The removable fragrance cartridge of claim 1, wherein the bottom surface is a flat surface.

9. The removable fragrance cartridge of claim 1, wherein the bottom surface has a plurality of surface features to allow secure placement of the fragrance cartridge within the imitation candle device.

10. The removable fragrance cartridge of claim 1, wherein the one or more fragrance materials is shaped as a disk for placement within the chamber.

11. The removable fragrance cartridge of claim 1, wherein the one or more fragrance materials is a fragrant liquid.

12. The removable fragrance cartridge of claim 1, wherein the top surface includes one or more gaps that separate at least some of the plurality of surface features.

13. The removable fragrance cartridge of claim 1, wherein the surface features include one or more of the following: a bump, a ridge, a protrusion, a channel, or a relief.

14. The removable fragrance cartridge of claim 1, further comprising a light.

15. The removable fragrance cartridge of claim 1, further comprising at least a section of a push button control switch.

16. A flameless electronic candle, comprising:
   a body including a cavity for housing a plurality of components of the flameless electronic candle;
   one or more light sources operably configured in the body;
   a removable fragrance cartridge disposed within the flameless electronic candle,
   wherein the fragrance cartridge comprises,
      a top surface including one or more holes to provide one or more pathways for diffusion of a fragrance from an interior of the fragrance cartridge to an area outside of the fragrance cartridge, the top surface including a plurality of surface features to further assist with diffusion of the fragrance;
      a bottom surface;
      an outer sidewall extending between the top surface and the bottom surface;
      an opening in the top surface defined by an inner sidewall extending between the top surface and the bottom surface, the opening formed at a central location of the fragrance cartridge such that, upon placement into the imitation candle device, the opening is positioned below an illuminated element protruding from a top section of the imitation candle device; and
      a chamber defined by the top surface, the bottom surface, the inner sidewall, and the outer sidewall, wherein the chamber comprises one or more fragrance materials.

17. The flameless electronic candle of claim 16, further comprising, a push button control switch to allow the activation of a scent mode, wherein the push button control switch is at least partially extending outwardly from the fragrance cartridge.

18. The flameless electronic candle of claim 16, further comprising, a heating element thermally coupled to the fragrance cartridge to facilitate dissemination of the fragrance materials.

19. The removable fragrance cartridge of claim 16, wherein the one or more holes are shaped as a circular opening.

20. The removable fragrance cartridge of claim 16, wherein the one or more holes have a diameter that is between five and ten percent of the outer diameter of the fragrance cartridge.

21. The removable fragrance cartridge of claim 16, wherein the one or more holes have a diameter between about two millimeters and twenty millimeters.

22. The removable fragrance cartridge of claim 16, further comprising one or more holes in the outer sidewall between the top surface and the bottom surface.

23. The removable fragrance cartridge of claim 16, wherein the opening extends through both the top and bottom surfaces.

24. The removable fragrance cartridge of claim 16, wherein the bottom surface has a plurality of surface features to allow secure placement of the fragrance cartridge within the imitation candle device.

25. The removable fragrance cartridge of claim 16, wherein the one or more fragrance materials is shaped as a disk for placement within the chamber.

26. The removable fragrance cartridge of claim 16, wherein the one or more fragrance materials is a fragrant liquid.

27. The removable fragrance cartridge of claim 16, wherein the top surface includes one or more gaps that separate at least some of the plurality of surface features.

28. The removable fragrance cartridge of claim 16, wherein at least one of the one or more light sources is integrated as part of the fragrance cartridge.

29. The removable fragrance cartridge of claim 16, further comprising at least a section of a push button control switch.

\* \* \* \* \*